(12) United States Patent
Robinson

(10) Patent No.: US 10,543,106 B2
(45) Date of Patent: Jan. 28, 2020

(54) INSERTER WITH IMPACT AND ROTATIONAL DRIVE ADVANCEMENT AND IMPLANT HOLDER WITH IMPLANT AUTO RELEASE

(71) Applicant: Alphatec Spine, Inc., Carlsbad, CA (US)

(72) Inventor: Scott Robinson, Encinitas, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 388 days.

(21) Appl. No.: 15/478,878

(22) Filed: Apr. 4, 2017

(65) Prior Publication Data

US 2017/0281365 A1    Oct. 5, 2017

Related U.S. Application Data

(60) Provisional application No. 62/318,426, filed on Apr. 5, 2016, provisional application No. 62/318,434, filed on Apr. 5, 2016.

(51) Int. Cl.
| | | |
|---|---|---|
| A61B 17/58 | (2006.01) | |
| A61B 17/60 | (2006.01) | |
| A61F 2/00 | (2006.01) | |
| A61F 2/46 | (2006.01) | |
| A61B 17/02 | (2006.01) | |

(52) U.S. Cl.
CPC .......... *A61F 2/4611* (2013.01); *A61B 17/025* (2013.01); *A61B 17/0206* (2013.01); *A61B 2017/0256* (2013.01)

(58) Field of Classification Search
CPC combination set(s) only.
See application file for complete search history.

(56) References Cited

U.S. PATENT DOCUMENTS

2013/0226244 A1\*  8/2013  Davenport ............ A61F 2/4465
606/279

\* cited by examiner

*Primary Examiner* — Sameh R Boles
(74) *Attorney, Agent, or Firm* — Honigman LLP

(57) ABSTRACT

An instrument with an implant holder disposed between a pair of tongs is provided. The implant holder may include a sleeve mechanically coupled to a distal end of a drive shaft and a pair of arms pivotably disposed within the sleeve. Movement of the sleeve in the distal direction pivots the pair of arms towards each other to grip the implant and movement of the sleeve in the proximal direction pivots the arms away from each other to automatically release the implant from the implant holder. The instrument may also include a dual mode drive shaft advancement mechanism that allows the implant holder to be advanced via an impact on the drive shaft from a tool such as a hammer or by rotation of the drive shaft.

18 Claims, 9 Drawing Sheets

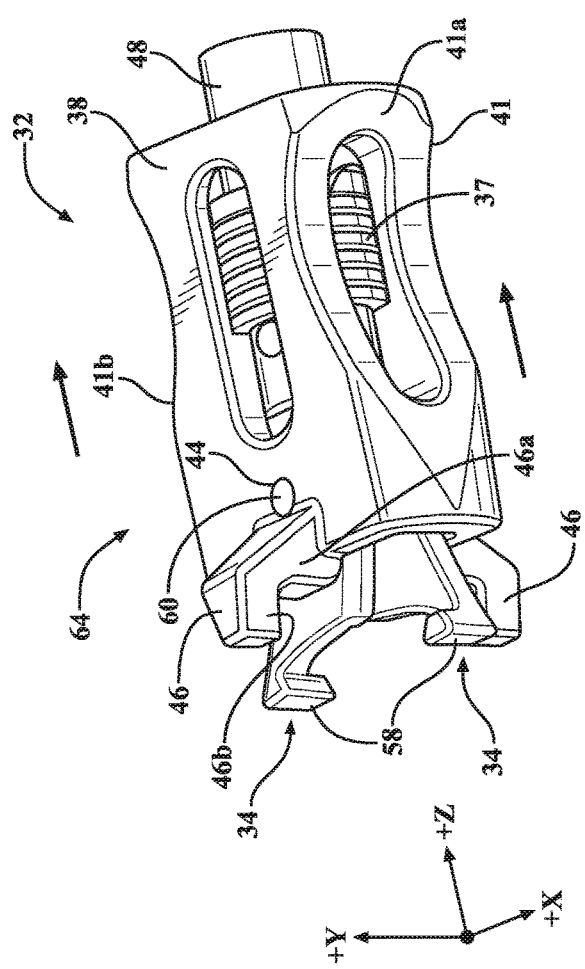
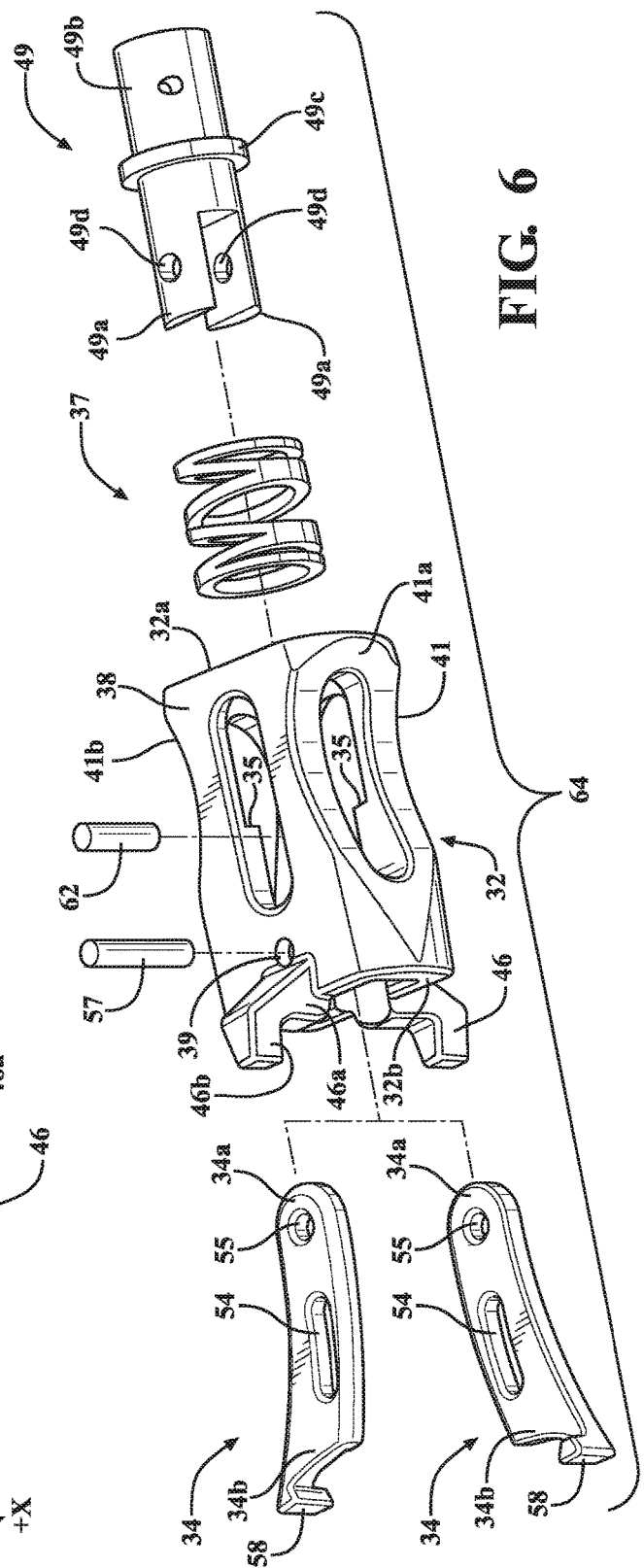
FIG. 5
FIG. 6

INSERTER WITH IMPACT AND ROTATIONAL DRIVE ADVANCEMENT AND IMPLANT HOLDER WITH IMPLANT AUTO RELEASE

CROSS-REFERENCE TO RELATED APPLICATIONS

This application claims priority of U.S. Provisional Patent Application Ser. No. 62/318,426 filed on Apr. 5, 2016, and U.S. Provisional Patent Application Ser. No. 62/318,434 filed on Apr. 5, 2016, both of which are incorporated herein in their entirety by reference.

BACKGROUND OF THE INVENTION

Inserters for inserting implants during spine surgery are currently known and used. The inserters include a drive shaft configured to introduce the implant into the surgical site. The inserters further include an implant holder configured to grip the implant as the implant is delivered to the surgical site.

During insertion, the vertebral bodies superior and inferior of the affected disc space are held apart (distracted) while an implant/spacer is placed there between. Often, this requires the use of at least two instruments, e.g., one instrument that distracts the superior and inferior vertebral bodies and another instrument that inserts the implant there between.

In addition, there are two common methods by which the implant is placed in the disc space. A first method is by impaction whereas the rate and position of the implant being inserted is dependent on an impaction force the surgeon applies to the inserter. A second method is to advance the implant by a more controlled or graduated method, such as rotation of a drive shaft to which the implant is secured. Also, there are currently two types of inserters. A first type of inserter facilitates the impaction force delivery method of the implant. The second type of inserter facilitates the controlled or graduated delivery method of the implant.

Once the implant is delivered or inserted between adjacent vertebras a release mechanism is actuated in order to disengage the implant from the inserter. The actuation of the release mechanism may require an assistant to hold the inserter in place.

Accordingly, it remains desirable to have an instrument for performing distraction and insertion with an impact delivery method and a controlled or graduate delivery method so as to reduce the number of instruments used in a surgical procedure. It also remains desirable to have an instrument which automatically releases the implant after the implant has been delivered to the surgical site so as to eliminate the need for an assistant.

SUMMARY OF THE INVENTION

An instrument for distracting a surgical site and inserting an implant is provided. The instrument includes a handle, a drive shaft disposed within the handle and a pair of tongs fixed to a distal end of the handle.

In embodiments, the instrument includes an implant holder disposed between the pair of tongs. The implant holder may include a sleeve mechanically coupled to a distal end of the drive shaft and a pair of arms rotatably disposed within the sleeve. Movement of the sleeve in the distal direction pivots the pair of arms towards each other to grip the implant and movement of the sleeve in the proximal direction pivots the arms away from each other to automatically release the implant from the implant holder. Advancement of the implant holder in a distal direction spreads the tongs apart from each other to distract the surgical site while the implant is delivered to the surgical site. Once the implant is positioned in the surgical site, further advancement of the pair of arms distally relative to the sleeve pivots the arms away from each other to automatically release and eject the implant from the implant holder. A slot pin fixed may be fixed to the sleeve and extend through an elongated slot in each of the pair of arms and a pivot pin may extend through a pivot aperture through each of the pair of arms such the pair of arms are rotatably attached to the distal end of the drive shaft. The slot pin may slide within the elongated slot of each of the pair of arms such that the pair of arms pivot about the pivot pin inwardly towards each other when the sleeve moves in the distal direction relative to the pair of arms and the arms pivot outwardly away from each other when the sleeve moves in the proximal direction relative to the pair of arms. A biasing member may be included and be configured to urge the sleeve in the distal direction. The biasing member may be positioned between the distal end of the drive shaft and an inner ledge of the sleeve.

In other embodiments, the instrument includes a drive shaft advancement mechanism configured to threadingly engaged the drive shaft in a first position and threadingly disengaged the drive shaft in a second position. The drive shaft advances in a distal direction or proximal direction upon rotation of the drive shaft when the drive shaft advancement mechanism is in the first position and the drive shaft advances from a blow from a tool such as a hammer when the drive shaft advancement mechanism is in the second position. The drive shaft advancement mechanism may include an engagement piece with at least one tooth configured to engage threads on the drive shaft when the drive shaft advancement mechanism is in the first position. The drive shaft advancement mechanism may also include a support member with a pair of support sleeves and an engagement piece positioned between the pair of support sleeves. The drive shaft advancement mechanism may include a lever configured to move the engagement piece between the first position and the second position. The lever may be pivotally coupled to the support member about a fulcrum pin with a proximal end of the lever extending from the handle and a distal end pivotally coupled to the engagement piece such that the lever pivots about the fulcrum pin to move the engagement piece from the first position to the second position. A biasing member may be included. The biasing member urges the drive shaft engagement mechanism into the first position such that the engagement piece with the at least one tooth is engaged with the thread on the drive shaft.

In still other embodiments, the instrument includes a handle, a threaded drive shaft disposed in the handle, a pair of tongs fixed to a distal end of the handle, a drive shaft advancement mechanism and an implant holder. The drive shaft advancement mechanism is configured to threadingly engage the drive shaft in a first position and threadingly disengaged the drive shaft in a second position. The drive shaft advances in a distal direction or proximal direction upon rotation of the drive shaft when the drive shaft advancement mechanism is in the first position and the drive shaft advances with a blow from a tool such as a hammer when the drive shaft advancement mechanism is in the second position. The implant holder is slidably disposed between the pair of tongs and may include a sleeve mechanically coupled to a distal end of the drive shaft and a pair of arms pivotably disposed within the sleeve. Movement of the sleeve in the distal direction pivots the pair of arms towards each other to grip the implant and movement of the sleeve in the proximal direction pivots the arms away from each other to release the implant from the implant holder. Also, advancement of the drive shaft in the distal direction spreads the tongs apart from each other to distract the surgical site while the implant is delivered to the surgical site. Once the implant is positioned in the surgical site, further advancement of the pair of arms distally relative to the sleeve pivots the arms away from each other to automatically release and eject the implant from the implant holder.

These and additional features provided by the embodiments described herein will be more fully understood in view of the following detailed description, in conjunction with the drawings.

BRIEF DESCRIPTION OF THE DRAWINGS

A better understanding of the present invention will be had upon reference to the following detailed description when read in conjunction with the accompanying drawings wherein like reference characters refer to like parts throughout the several views and in which:

FIG. 5 is perspective view of an implant holder according to one or more embodiments disclosed and described herein;

FIG. 6 is an exploded view of the implant holder in FIG. 5;

DETAILED DESCRIPTION OF THE INVENTION

Figure 1:
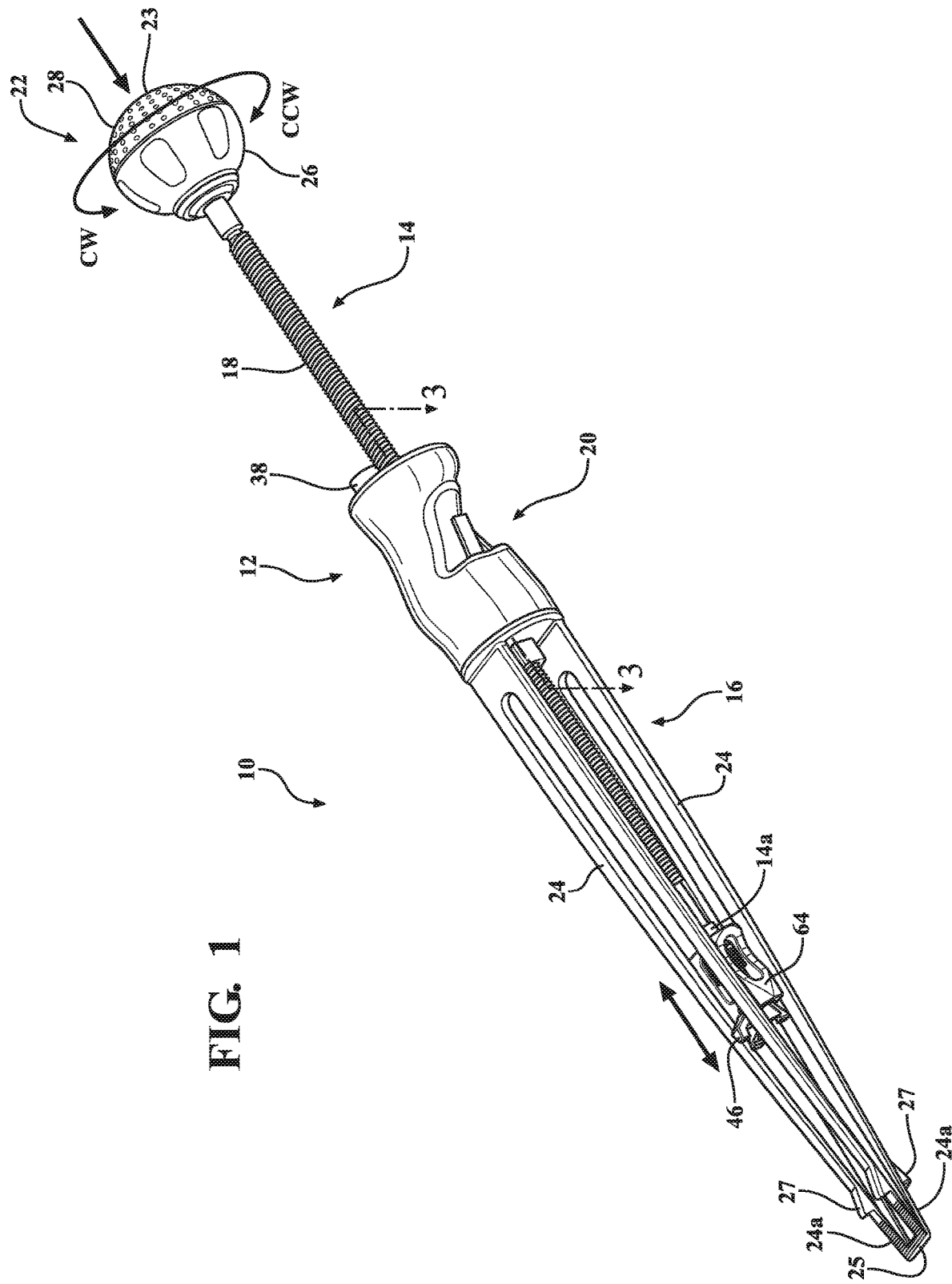
FIG. 1 is a perspective view of an instrument according to one or more embodiments disclosed and described herein.

An instrument (also referred to as an "inserter") for distracting a surgical site and inserting an implant is provided. The instrument reduces the number of instruments used to insert an implant by performing both distraction functions and insertion functions. Further, the insertion of the implant may be done by or using two implant advancement methods with one of the methods using an impact to drive the implant to the surgical site and another method using a controlled or graduated advancement to deliver the implant to a precise location at the surgical site. The instrument may also be configured to automatically release the implant once the implant is positioned at the precise location at the surgical site. The instrument facilitates the surgical procedure by eliminating the need for an assistant to help hold the instrument in place while the surgeon actuates an implant release mechanism.

In embodiments, the instrument includes a handle, a drive shaft, a pair of tongs and a drive shaft advancement mechanism. A proximal end of the drive shaft includes a surface configured to receive a blow from a tool such as a hammer and the drive shaft advancement mechanism is configured to allow the drive shaft to axially advance in a distal direction towards a surgical site as a result from the blow from the tool. Also the drive shaft includes threads and the drive shaft advancement mechanism may selectively engage the threads such that rotation of the drive shaft advances the drive shaft proximally or distally with respect to the handle. In such a manner the implant may be introduced into the surgical site with incremental precision.

In other embodiments, the instrument includes a handle, a drive shaft, a pair of tongs and an implant holder that automatically releases an implant once the implant has been introduced into the surgical site. The implant holder is slidably disposed between the pair of tongs and mechanically coupled to a distal end of the drive shaft. Advancement of the drive shaft, and thus the implant holder, in a distal direction spreads the tongs apart from each other and distracts the surgical site while the implant is delivered to the surgical site. When the implant holder abuts against the surgical site, e.g., abuts against two adjacent vertebras at the surgical site, and the drive shaft is further advanced in a distal direction, the implant holder automatically releases the implant.

In still other embodiments, the instrument includes a handle, a drive shaft, a pair of tongs, a drive shaft advancement mechanism and an implant inserter. As noted above, a proximal end of the drive shaft includes a surface configured to receive a blow from a tool such as a hammer and the drive shaft advancement mechanism is configured to allow the drive shaft to axially advance resulting from the blow for the tool. Also, the drive shaft includes threads and the drive shaft advancement mechanism may selectively engage threads on the drive shaft such that rotation of the drive shaft advances the drive shaft proximally or distally with respect to the handle. The implant holder is slidably disposed between the pair of tongs and mechanically coupled to a distal end of the drive shaft. Advancement of the drive shaft, and thus the implant holder, in a distal direction spreads the tongs apart from each other and distracts the surgical site while the implant is delivered to the surgical site. When the implant holder abuts against the surgical site, e.g., abuts against two adjacent vertebras at the surgical site, and the drive shaft is further advanced in a distal direction, the implant holder automatically releases the implant.

Figure 2:
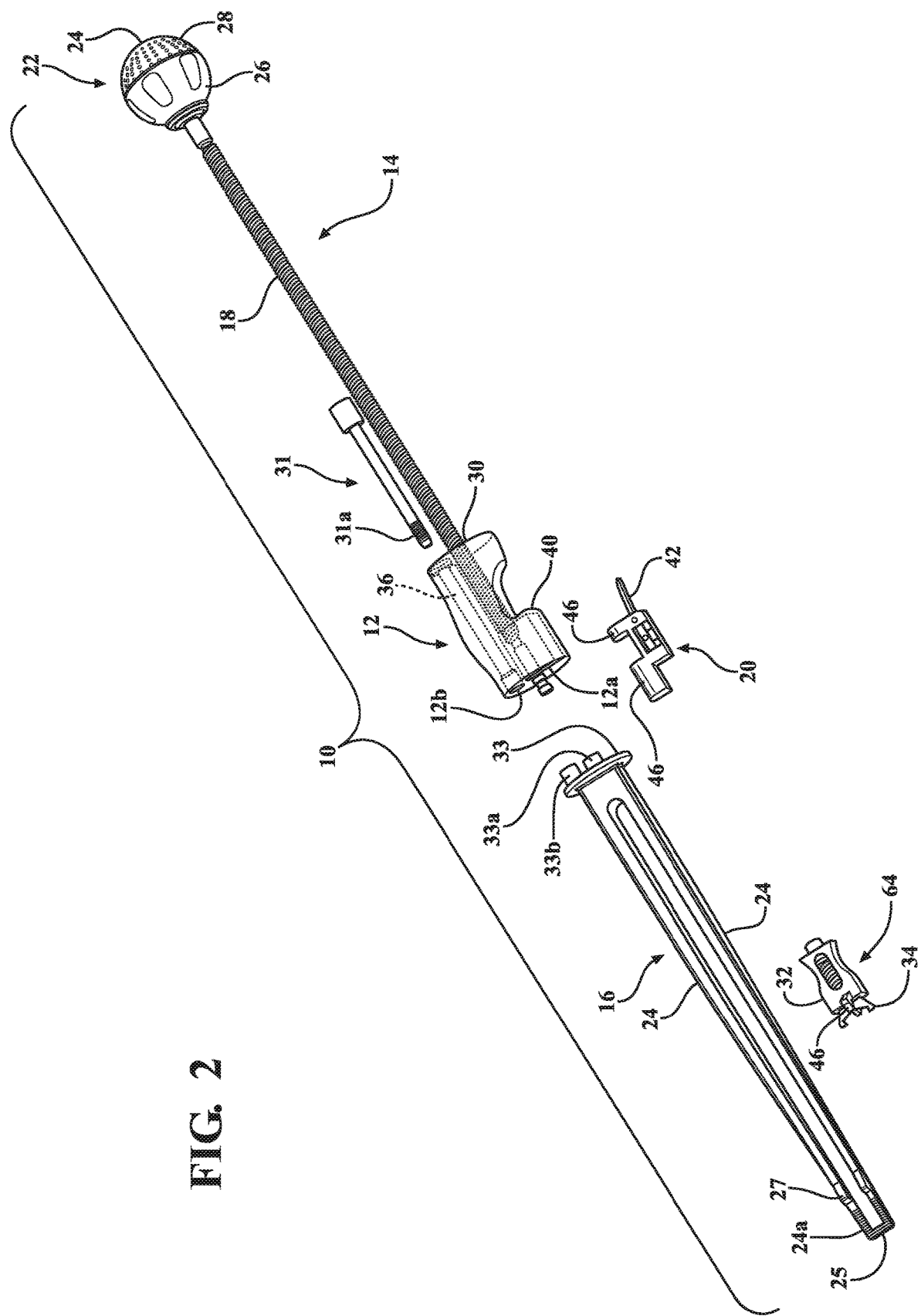
FIG. 2 is an exploded view of the instrument in FIG. 1.

With reference now to FIGS. 1 and 2 an illustrative embodiment of the instrument 10 is provided. The instrument 10 includes a handle 12, a drive shaft 14 and a pair of tongs 16. A base 33 may be positioned between the handle 12 and the pair of tongs 16 and an implant holder 64 configured to slide between the pair of tongs as illustrated by the double-headed arrow in the FIG. 1 may be included. In embodiments, the handle 12 is fixed to a proximal end or proximal side of the base 33 and the pair of tongs 16 are fixed to a distal end or distal side of the base 33. As used herein, the term "distal end" or "distal face" refers to an end or face that is proximate to a surgical site and the term proximal end" or "proximal face" refers to an end that is proximate to a user of the instrument facing the surgical site. Also, the term "distal direction" or "distally" refers to a direction from the user of the instrument towards a surgical site and the term "proximal direction" or "proximally" refers to a direction from the surgical site to the user of the instrument. Accordingly, the pair of tongs 16 extend distally from the handle 12. The drive shaft 14 includes a proximal end with a knob 22 and a distal end 14a attached to an implant holder 64 discussed in greater detail below. A proximal end of the knob 22 may include an impact pin 23 configured to receive a blow from a tool such as a hammer (not shown). A distal end of the knob 22 may be fixed to the proximal end of the drive shaft 14 such that rotation of the knob 22 rotates the drive shaft 14. The knob 22 may further include ribs 26 and raised edges 28 to assist in gripping of the knob 22 by a user so as to facilitate the rotation of the knob 22 and drive shaft 14.

The drive shaft 14, pair of tongs 16 and/or base 33 (shown in FIG. 2) may be formed of a polyetheretherketone, titanium, stainless steel, or any other material having sufficient structural rigidity to support implantation of the implant and which is also approved for medical use. The knob 22 may be formed of a resilient material such as plastic. The impact pin 23 may be formed of a durable and rigid material configured to withstand the impact of the tool.

The handle 12 has an outer surface dimensioned to be gripped or grasped by a user and has a through-bore 30 for which the drive shaft 14 is disposed. The handle 12 includes a pair of mating features 12a, 12b for coupling to the base 33. In particular, the base 33 may have male ends 33a, 33b configured to be inserted into respective mating features 12a, 12b of the handle 12. The handle 12 may include a through-hole 36 for which a securing pin 31 may be inserted so as to secure the handle 12 to the base 33. For example, the male end 33b may be in the form of a cylindrical wall with an internal thread (now shown) that is complementary to an external thread 31a on the distal end of the securing pin 31 such that the securing pin 31 may be threadingly engaged with the male end 33b thereby securing the handle 12 to the base 33. Although FIG. 2 depicts only one through-hole 36 and securing pin 31 for securing the handle 12 to the base 33, it should be understood that more than one through-hole 36 and securing pin 31 for securing the handle 12 to the base 33. In the alternative or in addition to, other securement mechanisms may be used to secure the handle 12 to the base 33, illustratively including but not limited to clips, adhesives, tongue-in-groove mating components, and the like.

Figure 3:
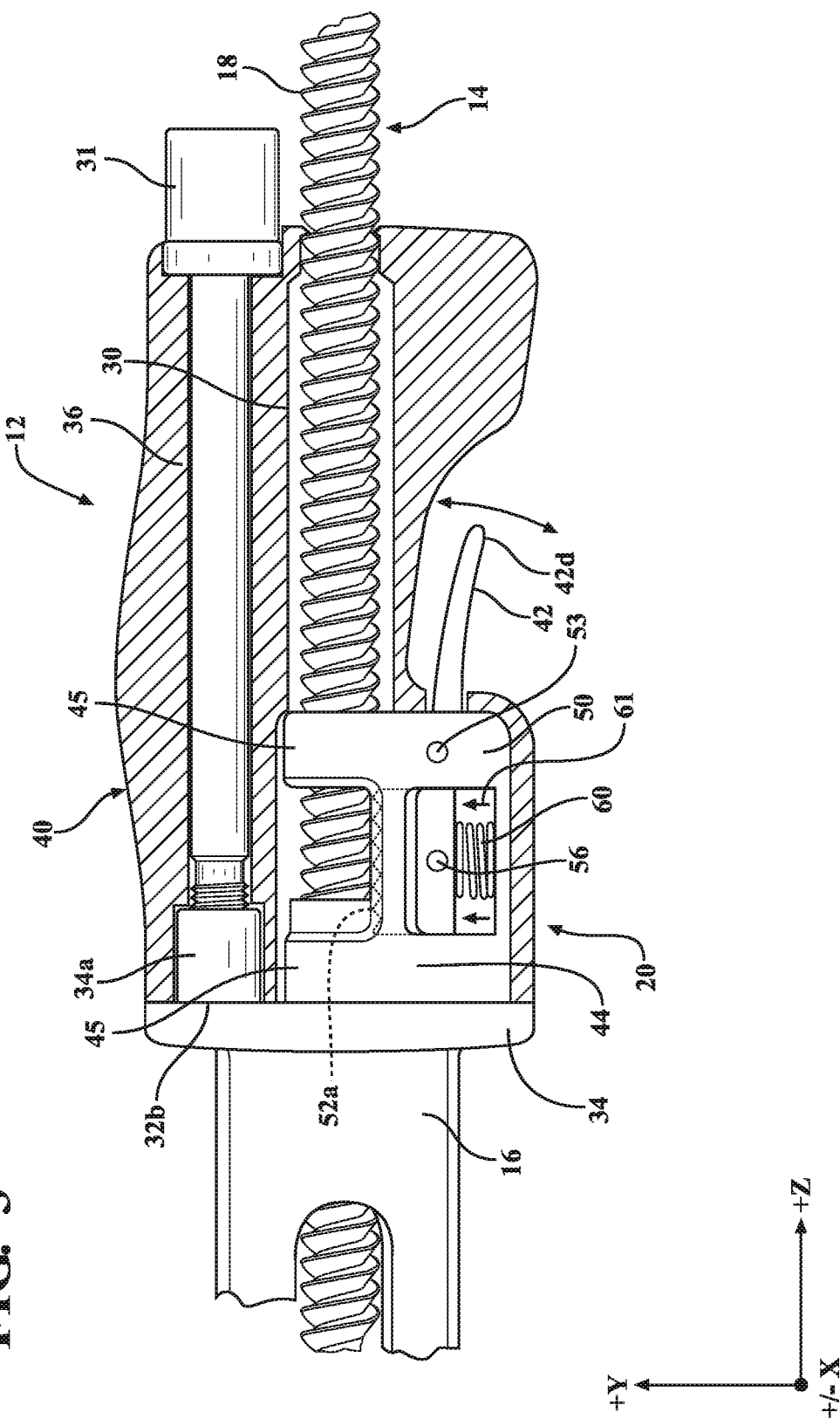
FIG. 3 is an isolated cross-sectional view of a handle with a drive shaft advancement mechanism according to one or more embodiments disclosed and described herein shown in FIG. 1 taken along line 3-3.

Referring now to FIGS. 2 and 3, the handle 12 includes a housing 40 configured to hold a drive shaft advancement mechanism 20. Accordingly, the handle 12 may function as both a structure for gripping and manipulating the instrument 10 and as a housing for containing the drive shaft advancement mechanism 20. Particularly, the handle 12 includes the through-bore 30 for which the drive shaft 14 is disposed and the securing pin 31 for coupling the handle 12 to the base 33. A lever 42, mechanically coupled to the drive shaft advancement mechanism 20, projects out of the handle 12 and is configured to disengage the drive shaft advancement mechanism 20 from threaded engagement with the drive shaft 14 as discussed in greater detail below.

Figure 4:
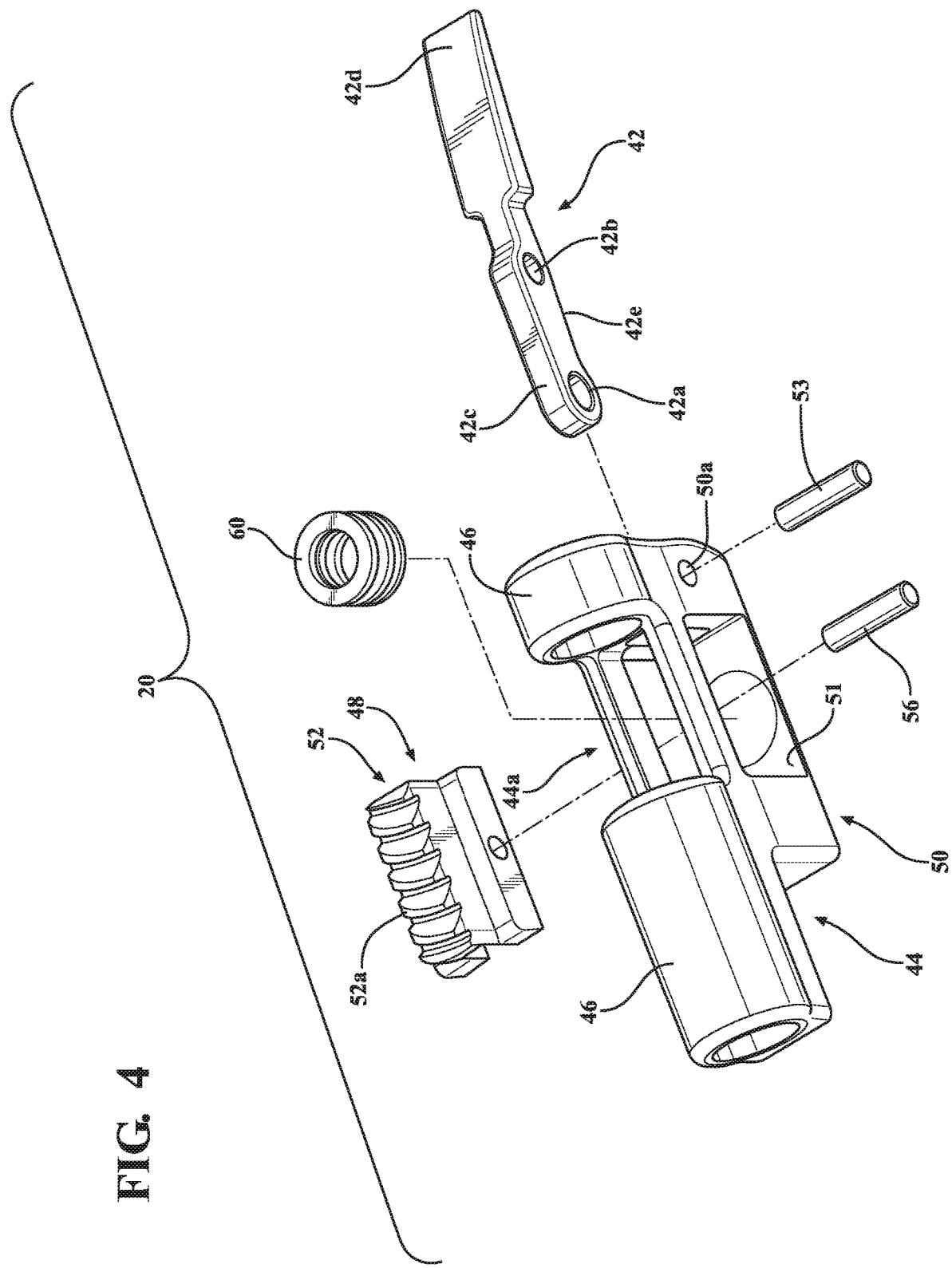
FIG. 4 is an exploded view of the drive shaft advancement mechanism in FIG. 3.

Referring now to FIGS. 3 and 4, an exemplary embodiment of the drive shaft advancement mechanism 20 is provided. The drive shaft advancement mechanism 20 is configured to engage and disengage a thread 18 (also referred to herein as "threads") of the drive shaft 14, i.e., the drive shaft advancement mechanism 20 is a dual mode advancement mechanism with one mode being engaged with the threads 18 of the drive shaft 14 and one mode being disengaged from the threads 18 of the drive shaft 14. In one mode of operation, the drive shaft 14 may be rotated so as to axially advance distally towards the surgical site and proximally away from the surgical site. In another mode of operation, the drive shaft advancement mechanism 20 is configured for the drive shaft 14 to axially advanced without rotation of the drive shaft, e.g., by impaction of a tool such as a hammer.

The drive shaft advancement mechanism 20 may include a support member 44 having a pair of support sleeves 45 through which the drive shaft 14 is disposed, i.e., the pair of support sleeves 45 are configured to hold the drive shaft 14. The pair of support sleeves 45 are spaced apart from each other so as to accommodate an engagement piece 48 there between. The support member 44 further includes a mounting portion 50 configured to hold the engagement piece 48. The engagement piece 48 includes a tooth section 52 with at least one tooth 52a. In embodiments, the tooth section 52 has a plurality of teeth 52a. It should be understood that each of the teeth 52a are slanted so as to accommodate engagement of the teeth 52a with the threads 18 of the drive shaft 14.

The engagement piece 48 in FIG. 4 depicts the tooth section 52 and the lever 42 formed of two separate pieces with the tooth section 52 fixed to the lever 42 with an attachment pin 56. However, it should be appreciated that the engagement piece 48 and lever 42 may be formed as a single unit. The lever 42 is pivotably mounted to the mounting portion 50 by a fulcrum pin 53 about which the lever 42 pivots. The fulcrum pin 53 extends through a fulcrum hole 42b of the lever 42 and a lever hole 50a of the mounting portion 50 such that movement of the lever 42 as indicted by the double-headed arrow in FIG. 3 moves the engagement piece 48 in an up direction (+Y direction depicted in FIG. 3) or down direction (−Y direction). A biasing member 60 may be included and be disposed between an inner surface 51 of the mounting portion 50 and a back side 42e of the lever 42 so as to continuously urge the tooth section 52 of the engagement piece 48 into engagement with the threads 18 of the drive shaft 14 as illustrated by arrows 61 in FIG. 3. That is, the biasing member 60 urges a distal end 42c of the lever 42 in an up direction (+Y direction) such that the engagement piece 48 with the plurality of teeth 52a are urged towards and engaged with the threads 18 of the drive shaft 14. In such a position, the drive shaft 14 may be advanced axially relative to the handle 12 in the distal direction or proximal direction by rotation of the drive shaft 14 within the handle 12. Also, the drive shaft 14 may be advanced axially in the distal direction relative to the handle 12 by impacting the impact pin and driving the drive shaft 14 (without rotation) distally. That is, the plurality of teeth 52a are angled relative to the threads 18 of the drive shaft such that one-way advancement of the drive shaft 14 in the distal direction is allowed.

Applying an upward force (+Y direction) on a proximal end 42d of the lever, e.g., by a user grasping the handle 12 and pulling on the proximal end 42d of the lever in a direction toward the handle 12, pivots the distal end 42c away from the drive shaft 14 (−Y direction). Pivoting the distal end 42c of the lever 42 away from the drive shaft 14 moves the plurality of teeth 52a of the engagement piece 48 away and disengaged with the threads 18 of the drive shaft. In such a position, the drive shaft 14 may be axially displaced relative to the handle 12 in the distal direction or proximal direction without rotation of the drive shaft 14 within the handle 12 (herein referred to as "sliding" or "slide" within the handle 12). For example, with the engagement piece 48 disengaged from the drive shaft 14, the drive shaft 14 may slide through the handle 12 by pushing the knob 22 in the distal direction, and in the alternative or in addition to, impacting the impact pin 23 of the knob 22 with a tool such as a hammer to drive the drive shaft 14 in the distal direction. Also, the drive shaft 14 may slide through the handle 12 in the proximal direction by pulling on the knob 22 in the proximal direction.

Accordingly, the instrument 10 with the drive shaft advancement mechanism 20 provides for either sliding or rotational advancement of the drive shaft 14 along a length of the instrument 10. For example, the biasing member 60 urges the engagement piece 48 into the first position where the plurality of teeth 52a are engaged with the threads 18 of the drive shaft 14. It should be understood that with the engagement piece 48 in the first position the drive shaft 14 advances distally or proximally by rotation of the drive shaft 14 relative to the handle 12, but the drive shaft 14 cannot slide within the handle 12. In the alternative, upon grasping the handle 12 and pulling on the proximal end 42d of the lever 42, the engagement piece 48 moves into the second position where the plurality of teeth 52a are disengaged from the threads 18 of the drive shaft 14 such that the drive shaft 14 can slide (without rotation) within the handle 12.

Referring now to FIGS. 1, 5 and 6, an implant holder 64 fixedly mounted to the distal end 14a of the drive shaft 14 is depicted in FIG. 1, an isolated view of the implant holder 64 is depicted in FIG. 5 and an exploded view of the implant holder 64 is depicted in FIG. 6. The implant holder 64 is configured to engage an implant for delivery into the surgical site as discussed in greater detail below. The implant holder 64 is positioned between the pair of tongs 16 (FIG. 1), wherein a distal end portion of each tongs 16 is pressed against each other so as to form a single wedge shape or edge that may be placed within a surgical site, e.g., within and between two adjacent vertebras. Each of the tongs 16 is illustratively shown as a pair of elongated stems 24 spaced apart from each other having an end bar 25 extending between distal ends 24a of the elongated stems 24 so as to form a closed end. A stop 27 spaced apart from the end bar 25 is formed on each of the pair of elongated stems 24. The stops 27 are spaced apart from the distal end 24a of each elongated stem 24 so as to limit the advancement of the tongs 16 into the surgical site, e.g., to limit a distance which the distal ends 24a may advance between adjacent vertebras.

The advancement of the implant holder 64 between the tongs 16 spreads the tongs 16 away from each other so as to distract the surgical site, e.g., spread adjacent vertebras away from each other. The implant holder 64, and thus the implant, may be delivered to the surgical site by impacting the proximal end of the handle 12 as discussed above. When the stop 27 is positioned against adjacent vertebras, delivery of the implant to the surgical site may be done by either impacting the proximal end of the handle 12 or by rotation of the drive shaft 14 as discussed above.

The implant holder 64 is mechanically coupled to the distal end 14a of the drive shaft 14 such that axial movement of the drive shaft 14 in the distal direction towards the surgical site or in the proximal direction away from the surgical site results in movement of the implant holder 64 in the distal direction or proximal direction, respectively. The proximal end of the tongs 16 are shown spaced apart from each other so as to be clear of the implant holder 64 and as the drive shaft 14 advances the implant holder 64 distally between the tongs 16, the implant holder 64 engages inner surfaces of the tongs 16 and spreads the tongs 16 away from each other so as to distract the surgical site.

Referring particularly to FIGS. 5 and 6, an illustrative embodiment of the implant holder 64 is provided. The implant holder 64 includes a sleeve 32, a pair of arms 34 and a biasing member 37. The pair of arms 34 are pivotably disposed within the sleeve 32 and are configured to grip the implant. The biasing member 37 continuously urges the sleeve 32 in a distal direction so as to close the arms 34 together and thereby grip the implant. Thus, retraction of the sleeve 32 in a proximal direction relative to the pair of arms 34 as indicated by the arrows in FIG. 5 pulls the sleeve 32 back relative to the arms 34 so as to allow the arms 34 to open and receive the implant. For example, a user may grasp and urge the sleeve 32 in the proximal direction relative to the pair or arms 34, position an implant between the arms 34, and allow the biasing member 37 to urge the sleeve 32 in the distal direction and close the arms 34 together and grip the implant.

The sleeve 32 includes a proximal end 32a, distal end 32b, top wall 38, bottom wall 41, a pair of side walls 41a, 41b. The proximal open end 32a and an opposite distal end 32b are open. Each of the top wall 38, bottom wall 41 and side walls 41a, 41b have an opening. The top wall 38 and the bottom wall 41 include a slot hole 39 and the side walls 41a, 41b are contoured to facilitate the grip of the user. As shown in FIG. 1, the side walls 41a, 41b are accessible by the space between the pair of tongs 16. The sleeve 32 includes a pair of prongs 46 integrally formed on or rigidly attached to the distal end 32b of top and bottom walls 38, 41. The pair of prongs 46 extend distally from the distal end 32b of the sleeve 32 and have an offset portion 46a and an axial portion 46b. The offset portion 46a extends generally normal (+/−Y direction) to the top wall 38 and bottom wall 41 and the axial portion 46b extends generally parallel with the top wall 38 and bottom wall 41 (−Z direction). The offset portion 46a results in the axial portion 46b being spaced outwardly (+/−Y direction from the top wall 38 and bottom wall 41 such that the prongs 46 slide over and engage the end bars 25 at the distal ends 24a of the tongs 16 comprising the pair of elongated stems 24. Engagement of the prongs 46 with the end bars 25 limit advancement of the pair of elongated stems 24 in the distal direction relative to the sleeve 32 as discussed in greater detail below.

Each of the arms 34 have a proximal end 34a and distal end 34b, a pivot hole 55 proximate to the proximal end 34a, a gripping member 58 configured to engage the implant and a curved elongated slot 54 extending between the proximate end 34a and distal end 34b. The proximal ends 34a of each of the arms 34 are pivotally coupled to an arm attachment member 49. Particularly, the arm attachment member 49 includes a pair of support members 49a spaced apart from each other and the pair of arms 34 may be positioned between the pair of support members 49a. The pivot pin 62 extends through a pivot hole 49d within each of the support members 49a and the pivot hole 55 of each arm 34 such that the arms 34 are secured to the arm attachment member 49 and pivot about the pivot pin 62. Also, the arm attachment member 49 may have an annular rib 49c disposed on an outer surface 49b of the arm attachment member 49. A biasing member 37 may be mounted over the pair of support members 49a and abut against the annular rib 49c and an inner ledge 35 within the sleeve 32 such that the sleeve 32 is urged away from the annular rib 49c in the distal direction and the arms 34 are biased towards each other in a closed position. A slot pin 57 extends through slot holes 39 in the top wall 38, bottom wall 41 and curved elongated slots 54 in each of the arms 34. As the sleeve 32 and slot pin 57 move relative to the pair of arms 34 in the distal and proximal directions, the slot pin 57 slides within the curved elongated slots 54 in the distal and proximal directions, respectively.

Figure 7:
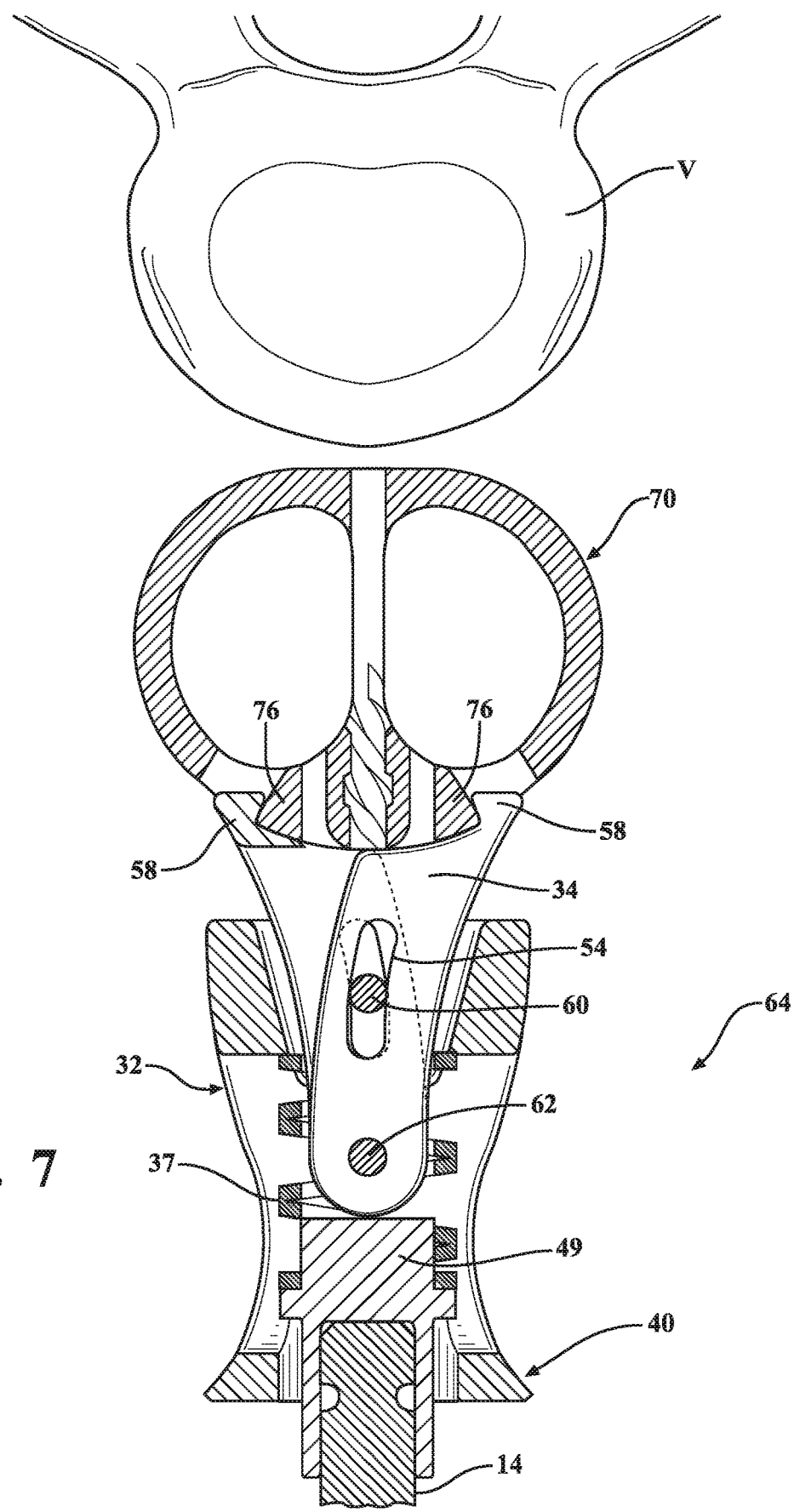
FIG. 7 is a cross-sectional view of the implant holder in FIG. 5 gripping an implant according to one or more embodiments disclosed and described herein, the implant being positioned proximate to a pair of vertebras.
Figure 8:
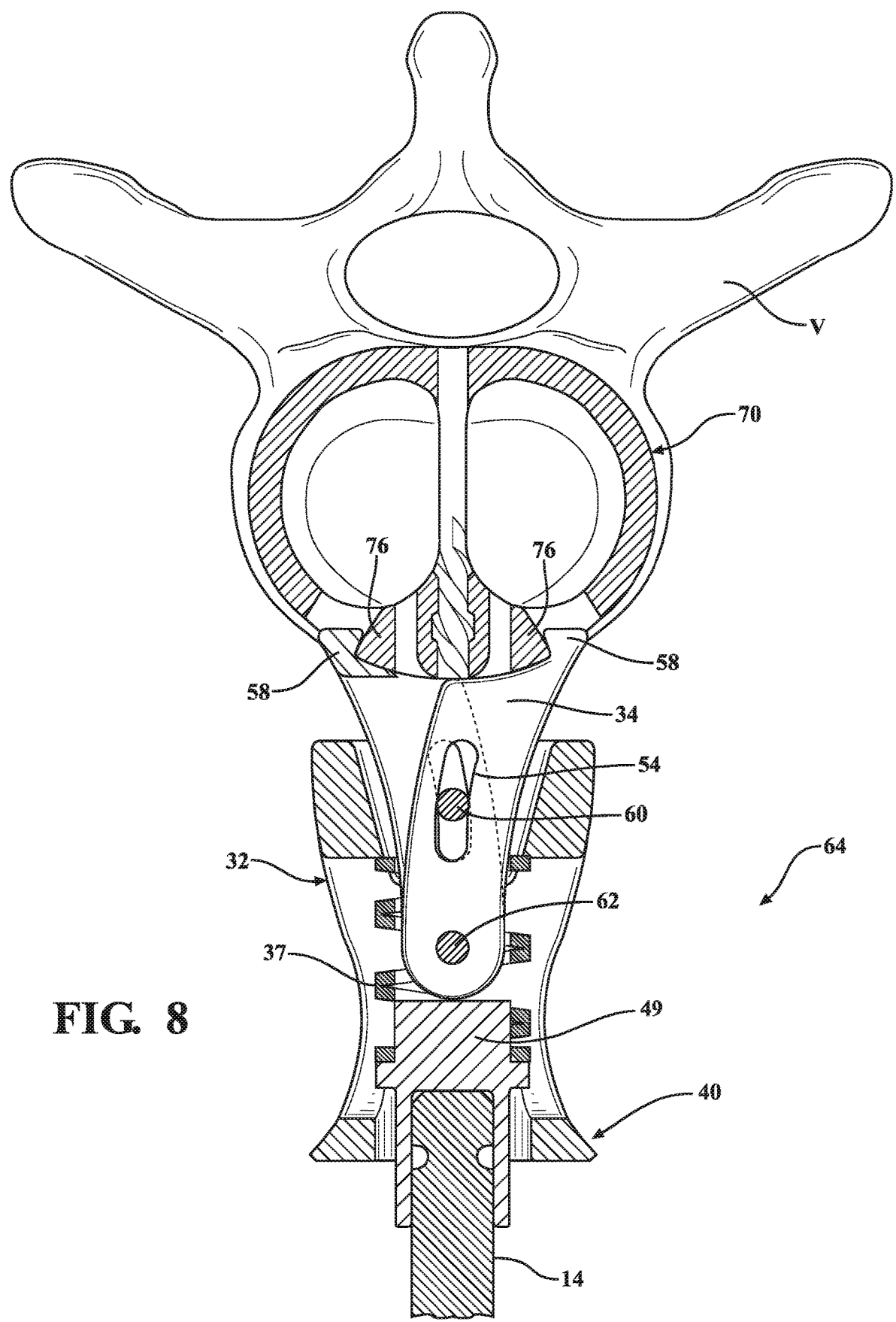
FIG. 8 is a view of the implant and implant holder in FIG. 7 with the implant inserted between the pair of vertebras.
Figure 9:
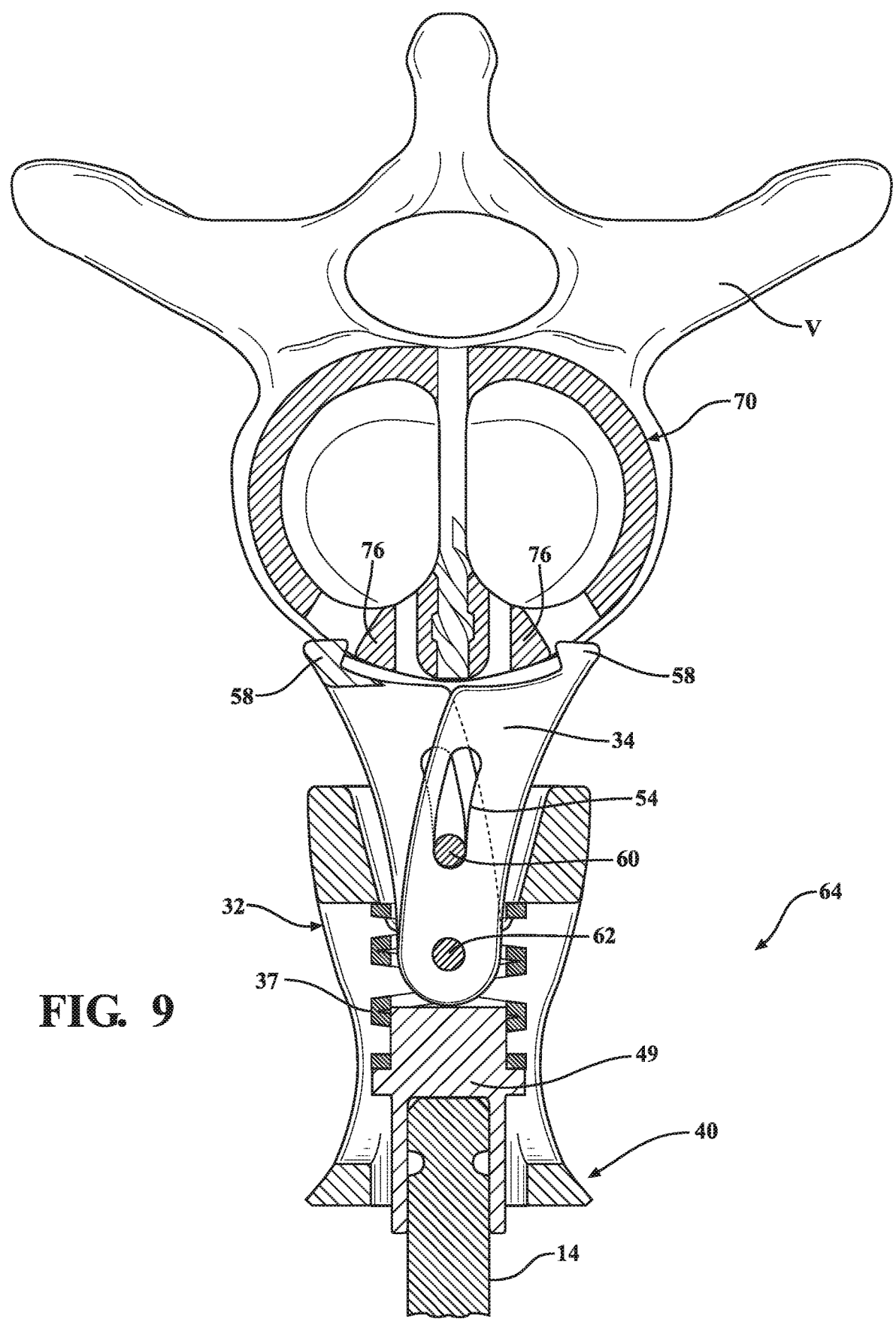
FIG. 9 is a view of the implant and implant holder in FIG. 8 with the implant inserted between the pair of vertebras and the implant holder releasing the implant.
Figure 10:
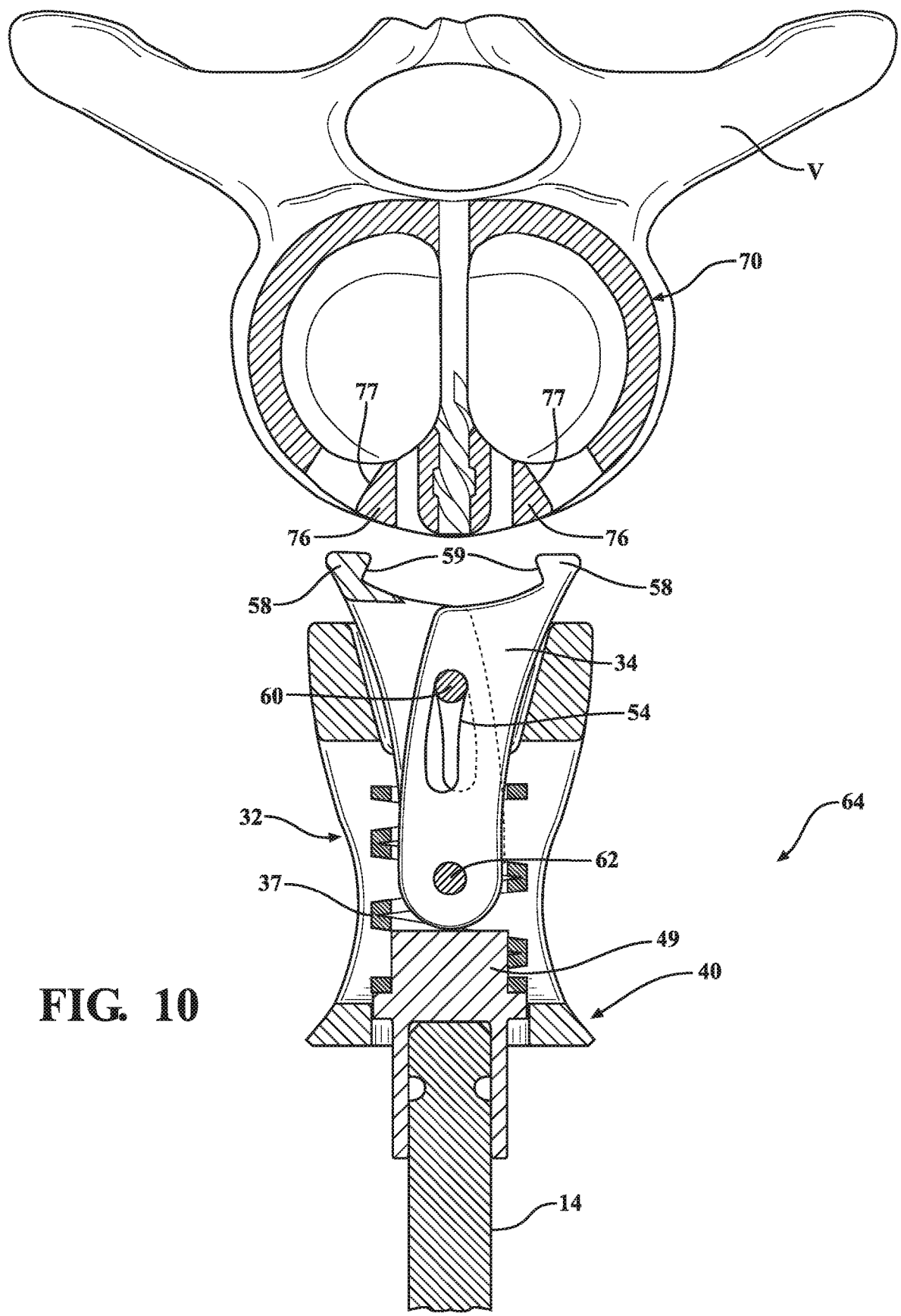
FIG. 10 is a view of the implant and implant holder in FIG. 9 with the implant released from the implant holder.

With reference now to FIGS. 7-10, FIG. 7 depicts the implant holder 64 gripping an implant 70 before the implant 70 is inserted between two adjacent vertebras V (only one vertebra V shown) with the gripping members 58 engaged with the flanges on the implant 70. FIG. 8 depicts the implant 70 inserted between the two vertebras V. FIG. 9 depicts the implant holder with the pair of arms 34 in the open position and the implant 70 released from the implant holder 64. As shown in FIG. 9 in comparison with FIG. 8, the pair of arms 34 have advanced distally relative to the sleeve 32 and the slot pint 60, i.e., the slot pin 60 has moved proximally within the curved elongated slots 54 resulting in the pair of arms 34 pivoting outwardly from each into the open position. FIG. 10 depicts the implant 70 inserted between the two adjacent vertebras and the implant holder 64 removed from the implant 70. As shown in FIG. 10 in comparison with FIG. 9, the pair of arms 34 have been advanced proximally relative to the sleeve 32 and the slot pint 60, i.e., the slot pin 60 has moved distally within the curved elongated slots 54 resulting in the pair of arms 34 pivoting inwardly towards each other into the closed position. FIG. 10 also illustrates inner surfaces 59 of the gripping members 58 being complimentary with outer surfaces 77 of the flanges 76 such that secure gripping of the implant holder 64 to the implant 70 is provided.

In operation, the sleeve 32 is moved in the proximal direction relative to the pair of arms 34 such that the arms pivot into the open position and the implant 70 is positioned between the gripping members 58. The sleeve is allowed to move in the distal direction and the gripping members engage flanges 76 of the implant 70 and the implant 70 is secured to the implant holder 70 (FIG. 7). The implant 70 is inserted between two adjacent vertebras to a desired position (FIG. 8) and the drive shaft is further advanced until the pair of arms pivot to the open positon and release the implant 70 (FIG. 9). The instrument 10 is then removed from the surgical leaving the implant 70 between the two adjacent vertebras (FIG. 10).

In embodiments, a method for using the instrument 10 includes a surgeon grapping the sleeve 32 of the implant holder 64 and sliding or moving the sleeve 32 in the proximal direction towards the handle 12. Movement of the sleeve 32 in the proximal direction pivots the pair of arms 34 outwardly from each other to the open position. The surgeon places the implant 70 between the pair of arms 34 such that the flanges 76 are positioned between the gripping members 58. The surgeon releases the sleeve 32 so as to allow the sleeve 32 to move in the distal direction, e.g., via being urged by the biasing member 60, which in turn pivots the pair of arms 34 inwardly towards each other such that the gripping members 58 engage the flanges 76 of the implant 70. The biasing member 60 provides a constant inward tension or bias of the gripping members 58 against the flanges 76 and the implant 70 is secured to the implant holder 64.

The surgeon inserts the distal ends 24a of the elongated stems 24 into an incision of a patient and advances the pair of tongs 16 to a position adjacent two adjacent vertebras. The surgeon applies pressure to the instrument in the distal direction and inserts the distal ends 24a between the two adjacent vertebras. The distal ends 24a are advance distally between the two adjacent vertebras until the stops 27 on the elongated stems 24 abut against the two adjacent vertebras. With the distal ends 24a within the surgical site, i.e., within and between the two adjacent vertebras, the drive shaft 14 is advanced in the distal direction. As noted above, the drive shaft 14 may be advanced in the distal direction by pushing or impacting the knob 22 in the distal direction when the drive shaft advancement mechanism 20 is disengaged from the threads 18 of the drive shaft 14 or by rotation of the drive shaft 14 when the drive shaft mechanism 29 is engaged with the threads 18. Advancement of the implant holder 64 positioned between the pair of tongs 16 in the distal direction spreads the pair of tongs 16 apart from each other thereby distracting the surgical site.

The implant holder 64 and implant 70 are advanced distally such that the implant 70 is inserted between the two adjacent vertebras and the prongs 46 of the sleeve 32 abut against the two adjacent vertebras. Pressure is applied to the instrument 10 in the distal direction to ensure the prongs 46 maintain contact with the two adjacent vertebras. Further rotation of the drive shaft 14 pulls the pair of tongs 16 in the proximal direction relative to the implant holder 64 (and relative to the two adjacent vertebras) until end bars 25 at the distal ends 24a of the elongated stems 24 engage the prongs 46 of the sleeve 32. After the prongs 46 engage the end bars 25, the sleeve 32 is in a fixed position relative to the pair of tongs 16 and further advancement of the distal end 14a of the drive shaft 14 in the distal direction moves the pair of arms 34 distally relative to the sleeve 32 and slot pin 57 such that the pair of arms 34 pivot outwardly from each other into the open position and release the implant 70. Once the implant 70 is released from the implant holder 64, the surgeon pulls the instrument 10 to in the proximal direction leaving the implant 70 between the adjacent vertebras. Accordingly, the instrument 10 provides an instrument that allows a surgeon to advance an implant towards a surgical site by impacting a distal end of drive shaft in a distal direction and/or by rotation of the drive shaft to incrementally advance the implant. The instrument 10 also allows the implant to be automatically released once properly inserted in the surgical site. It should be appreciated that the instrument 10 may be used as an instrument with a dual mode implant advancement mechanism, as an instrument with an automatic implant release mechanism, or as an instrument with a dual mode implant advancement mechanism and an automatic implant release mechanism.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

The invention claimed is:

1. An instrument for distracting a surgical site and inserting an implant, the inserter comprising:
   a handle;
   a drive shaft disposed within the handle;
   a pair of tongs fixed to a distal end of the handle; and
   an implant holder slidably disposed between the pair of tongs, the implant holder comprising a sleeve mechanically coupled to a distal end of the drive shaft and a pair of arms pivotably disposed within the sleeve, wherein:
   movement of the sleeve in a distal direction pivots the pair of arms towards each other to grip the implant and movement of the sleeve in a proximal direction pivots the arms away from each other to automatically release the implant from the implant holder; and
   advancement of the drive shaft in the distal direction spreads the pair of tongs apart from each other to distract the surgical site while the implant is delivered to the surgical site and automatically released from the implant holder.

2. The instrument of claim 1, further comprising a slot pin fixed to the sleeve and extending through a curved elongated slot in each of the pair of arms, and a pivot pin extending through a pivot hole through each of the pair of arms, wherein the slot pin slides within the curved elongated slot of each of the pair of arms such that the pair of arms rotate about the pivot pin inwardly towards each other when the sleeve moves in the distal direction and the pair of arms rotate outwardly away from each other when the sleeve moves in the proximal direction.

3. The instrument of claim 2, further comprising a biasing member configured to urge the sleeve in the distal direction.

4. The instrument of claim 3, wherein the biasing member is positioned between the distal end of the drive shaft and an inner ledge within the sleeve.

5. The instrument of claim 1, wherein:
the implant holder comprises an arm attachment member positioned at least partially within the sleeve and fixed to the distal end of the drive shaft, and a biasing member configured to urge the sleeve in the distal direction away from the arm attachment member;
each of the pair of arms comprise a curved elongated slot extending along a length of each arm;
the sleeve comprises a slot pin extending through the curved elongated slot of each of the pair of arms;
sliding of the slot pin within the curved elongated slots in the distal direction pivots the pair of arms towards each other; and
sliding of the slot pin within the curved elongated slots in the proximal direction pivots the pair of arms away from each other.

6. The instrument of claim 5, wherein a proximal end of each of the pair of arms is pivots mounted to the arm attachment member about a pivot pin such that the pair of arms pivot about the pivot pin when the slot pin slides within the curved elongated slot of each arm in the distal direction and proximal direction.

7. The instrument of claim 6, wherein the sleeve comprises a pair of prongs extending in the distal direction, the pair of prongs configured to abut against the surgical site as the implant is inserted into the surgical site.

8. The instrument of claim 1, wherein the drive shaft comprises external threads and the handle comprises internal threads such that rotation of the drive shaft relative to the handle in a first rotational direction displaces the implant holder in the distal direction and rotation of the drive shaft relative to the handle in a second rotational direction advances the implant holder in the proximal direction.

9. An instrument for distracting a surgical site and inserting an implant, the instrument comprising:
a handle;
a drive shaft with threads disposed within the handle, a distal end of the drive shaft configured to hold the implant and a proximal end of the drive shaft configured to receive a blow from a tool;
a pair of tongs fixed to a distal end of the handle; and
a drive shaft advancement mechanism configured to either threadingly engaged the drive shaft in a first position and threadingly disengaged the drive shaft in a second position, wherein the drive shaft advances in a distal direction or proximal direction upon rotation of the drive shaft when the drive shaft advancement mechanism is in the first position and the drive shaft advances from the blow from the tool when the drive shaft advancement mechanism is in the second position.

10. The instrument of claim 9, wherein:
the drive shaft advancement mechanism comprises a support member with a pair of support sleeves and an engagement piece positioned between the pair of support sleeves; and
an engagement piece with at least one tooth configured to engage the threads on the drive shaft when the drive shaft advancement mechanism is in the first position.

11. The instrument of claim 10, wherein the drive shaft advancement mechanism comprises a lever configured to move the engagement piece between the first position wherein the at least one tooth is engaged with the thread on the drive shaft and the drive shaft advances by rotation of the drive shaft and the second position wherein the at least one tooth is not engaged with the threads of the drive shaft and the drive shaft advances from the blow from the tool.

12. The instrument of claim 11, wherein the lever is pivotally coupled to the support member about a fulcrum pin with a proximal end of the lever extending from the handle and a distal end pivotally coupled to the engagement piece such that the lever rotates about the fulcrum pin to move the engagement piece from the first position to the second position.

13. An inserter for distracting a surgical site and inserting an implant, the inserter comprising:
a handle;
a drive shaft with threads disposed within the handle and a proximal end of the drive shaft configured to receive a blow from a tool;
a pair of tongs fixed to a distal end of the handle;
a drive shaft advancement mechanism configured to threadingly engaged the drive shaft in a first position and threadingly disengaged the drive shaft in a second position, wherein the drive shaft advances in a distal direction or proximal direction upon rotation of the drive shaft when the drive shaft advancement mechanism is in the first position and the drive shaft advances with the blow from the tool when the drive shaft advancement mechanism is in the second position; and
an implant holder fixed to a distal end of the drive shaft and slidably disposed between the pair of tongs, the implant holder comprising a sleeve mechanically coupled to the distal end of the drive shaft and a pair of arms pivotably disposed within the sleeve, wherein:
movement of the sleeve in the distal direction relative to the pair of arms pivots the pair of arms towards each other to grip the implant and movement of the sleeve in the proximal direction relative to the pair of arms pivots the arms away from each other to automatically release the implant from the implant holder; and
advancement of the implant holder in the distal direction spreads the pair of tongs apart from each other to distract the surgical site while the implant is delivered to the surgical site, and advancement of the drive shaft in the distal direction relative to the sleeve pivots the arms away from each other to automatically release the implant from the implant holder.

14. The inserter of claim 13, wherein:
the drive shaft advancement mechanism comprises a support member with a pair of support sleeves and an engagement piece positioned between the pair of support sleeves;

the drive shaft extends through the pair of support sleeves; and the engagement piece has at least one tooth configured to engage the threads on the drive shaft.

15. The inserter of claim 14, wherein the drive shaft advancement mechanism comprises a lever configured to move the engagement piece between the first position wherein the at least one tooth is engaged with the thread on the drive shaft and the drive shaft advances by rotation of the drive shaft within the pair of support sleeves and the second position wherein the at least one tooth is not engaged with the threads of the drive shaft and the drive shaft advances from the blow from the tool.

16. The inserter of claim 15, wherein the lever is pivotally coupled to the support member about a fulcrum pin with a proximal end of the lever extending from the handle and a distal end pivotally coupled to the engagement piece such that the lever rotates about the fulcrum pin to move the engagement piece from the first position to the second position.

17. The inserter of claim 13, further comprising:
a slot pin fixed to the sleeve and extending through a curved elongated slot in each of the pair of arms; and
a pivot pin extending through a pivot hole in a proximal end of each of the pair of arms;
wherein the slot pin slides within the curved elongated slot of each of the pair of arms such that the pair of arms rotate about the pivot pin inwardly towards each other to grip the implant when the sleeve moves in the distal direction relative to the pair of arms and the pair of arms rotate outwardly away from each other to automatically release the implant when the sleeve moves in the proximal direction relative to the pair of arms.

18. The insert of claim 13, wherein the sleeve comprises a pair of prongs extending from a distal end of the sleeve in the distal direction, the pair of prongs configured to abut against adjacent vertebras when advancement of the drive shaft in the distal direction spreads the pair of tongs apart from each other to distract the surgical site while the implant is delivered to the surgical site.

* * * * *